United States Patent [19]

Yamaguchi et al.

[11] Patent Number: 5,049,057

[45] Date of Patent: Sep. 17, 1991

[54] DEVICE FOR CONTINUOUSLY MEASURING AND CORRECTING TACKINESS OF SHEET OF UNVULCANIZED RUBBER MATERIAL

[75] Inventors: Youichi Yamaguchi, Hiratsuka; Shohei Nakayama, Odawara; Shigeru Shinoda, Chigasaki, all of Japan

[73] Assignee: The Yokohama Rubber Co., Ltd., Tokyo, Japan

[21] Appl. No.: 519,522

[22] Filed: May 4, 1990

[30] Foreign Application Priority Data

May 11, 1989 [JP] Japan ................... 1-116191

[51] Int. Cl.⁵ .............. B29C 7/00; G01B 5/00; G01N 19/04
[52] U.S. Cl. ................... 425/135; 73/150 R; 264/40.1; 264/340; 425/90; 425/169; 425/445
[58] Field of Search ............ 73/150 R, 150 A, 159; 264/40.1, 340, 341, 343; 425/135, 169, 225, 90, 317, 404, 445, 446

[56] References Cited

U.S. PATENT DOCUMENTS

| | | | |
|---|---|---|---|
| 2,762,219 | 9/1956 | Prentiss | 73/150 R |
| 2,960,865 | 11/1960 | Brown | 73/150 R |
| 3,436,963 | 4/1969 | Domen | 73/150 R |
| 3,559,475 | 2/1971 | Dillon | 73/150 R |
| 3,901,149 | 8/1975 | Schulte-Kulkmann | 73/150 R |
| 4,312,212 | 1/1982 | Clendenin | 73/150 R |

FOREIGN PATENT DOCUMENTS 57-63435 4/1982 Japan.

*Primary Examiner*—Jay H. Woo
*Assistant Examiner*—James P. Mackey
*Attorney, Agent, or Firm*—Armstrong, Nikaido, Marmelstein, Kubovcik, & Murray

[57] ABSTRACT

A device for continuously measuring and correcting a tackiness of a sheet of rubber material including a feeding unit for continuously feeding an unvulcanized rubber sheet along a flat support surface and a rotatable roller in contact with the unvulcanized rubber sheet, whereby the roller is rotated by the movement of the unvulcanized rubber sheet, and entrained in the sheet feed direction due to a tackiness of the unvulcanized rubber sheet. A load cell is connected to the roller via a linkage, for measuring a resistance to the rolling of the roller, i.e., a change of a position of the roller entrained in the sheet feed direction. The device also includes a correcting unit for correcting a tackiness of the sheet of unvulcanized rubber material, the correcting unit being controlled by a control element in response to an output from the measuring unit, in such a manner that the correcting unit acts on the surface of the unvulcanized rubber sheet of rubber material when an output from the measuring unit is outside a predetermined range of tackiness.

15 Claims, 7 Drawing Sheets

DEVICE FOR CONTINUOUSLY MEASURING AND CORRECTING TACKINESS OF SHEET OF UNVULCANIZED RUBBER MATERIAL

BACKGROUND OF THE INVENTION

1. Field of the Invention

The present invention relates to a device for continuously measuring and correcting a tackiness of a sheet of unvulcanized rubber material.

2. Description of the Related Art

The tackiness of an unvulcanized rubber material, such as a sheet of unvulcanized rubber material or a calendered unvulcanized rubber material is measured as a step for an improvement of a subsequent treatment of the rubber material. Conventional tackiness measuring devices use a pair of opposed adherent samples, which are pressed together and then one sample is peeled from the other. For example, Japanese Unexamined Patent Publication No. 57-63435 discloses a tackiness measuring device in which a lower adherent sample is firmly held in a stationary position and an upper sample is held around a periphery of a metal disk. The metal disk can be lowered or lifted at a constant speed, whereby the upper sample is pressed against the lower adherent sample by lowering the metal disk and the upper sample is peeled from the lower adherent sample by lifting the metal disk. A resistance force measured when the upper sample is peeled from the lower adherent sample is considered to represent a tackiness of the samples.

In conventional tackiness measuring devices, however, the samples must be prepared as cut pieces, and the measuring of the tackiness of a sheet of unvulcanized rubber material is usually carried out under controlled environmental conditions. Accordingly, it is not possible to continuously use conventional tackiness measuring devices on a rubber manufacturing line. Further, it is necessary to carry out repeated samplings and testings of the tackiness of the rubber material in a rubber manufacturing line, which leads to a need for labor-consuming work and variations of the resultant data due to discontinuity in the measuring process.

SUMMARY OF THE INVENTION

An object of the present invention is to provide a device for continuously measuring and correcting a tackiness of a sheet of unvulcanized rubber material, by which the tackiness of a sheet of unvulcanized rubber material can be continuously measured and corrected to an appropriate value, and thus the device can be used in a rubber manufacturing line.

Therefore, according to the present invention, there is provided a device for continuously measuring and correcting a tackiness of a sheet of unvulcanized rubber material, comprising a feeding means for continuously feeding a sheet of unvulcanized rubber material along a predetermined path in a predetermined direction; at least one rotatable roller in contact with the sheet of unvulcanized rubber material and having a central shaft extending perpendicular to the predetermined feeding direction; linkage means having a first end and a second end, the first end being operatively connected to the shaft of the roller; measuring means arranged at a fixed position on a stationary frame member and operatively connected to the second end of the linkage means for measuring a rolling resistance of the roller relative to the sheet of unvulcanized rubber material when the roller is in contact with the sheet of unvulcanized rubber material, the rolling resistance being representative of a tackiness of the sheet of unvulcanized rubber material; correcting means above to act on the surface of the sheet of unvulcanized rubber material, to correct the tackiness of the sheet of unvulcanized rubber material; and control means for controlling the correcting means in response to an output from the measuring means, such that the correcting means acts on the surface of the sheet of unvulcanized rubber material when an output from the measuring means is outside a predetermined range of tackiness and does not act on that surface when an output from the measuring means is within the predetermined range of tackiness.

BRIEF DESCRIPTION OF THE DRAWINGS

The present invention will become more apparent from the following description of the preferred embodiment with reference to the accompanying drawings; in which.

DESCRIPTION OF THE PREFERRED EMBODIMENTS

Figure 1:
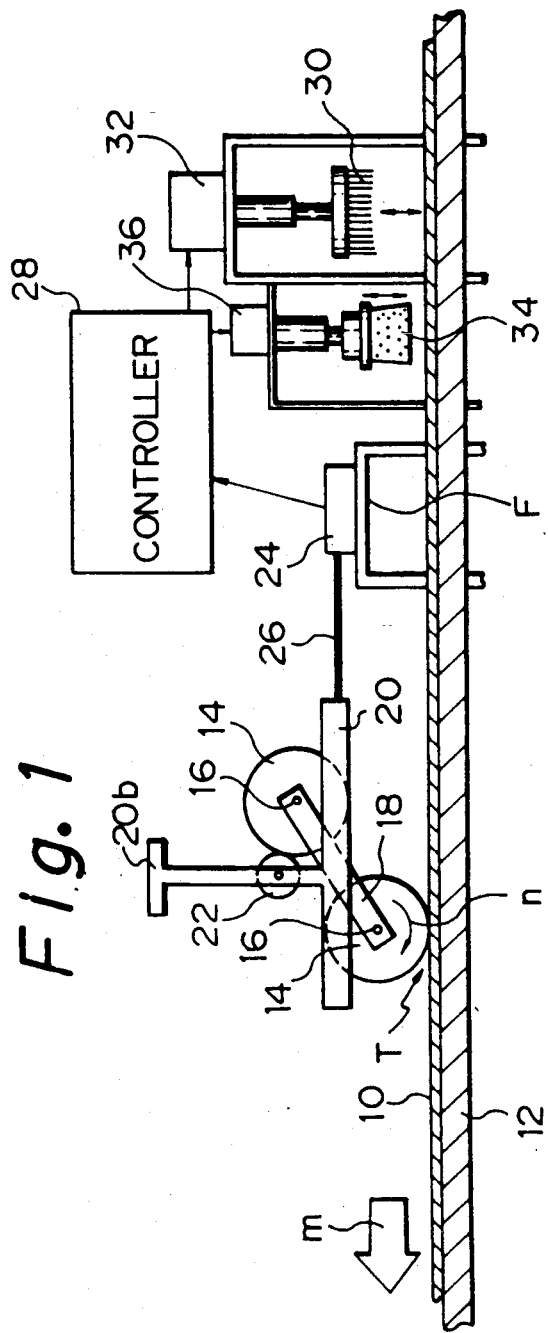
FIG. 1 is a side elevational view of a device for continuously measuring and correcting a tackiness of a sheet of unvulcanized rubber material according to the first embodiment of the present invention.

FIG. 1 shows a device for continuously measuring and correcting a tackiness of a sheet of unvulcanized rubber material according to the present invention. This device is arranged in a rubber manufacturing line which includes a feeding means (not shown) for feeding a sheet or web 10 of unvulcanized rubber material along a support member 12 at a constant speed in the direction as shown by the arrow m. The support member 12 is stationary at least in the illustrated region of the rubber manufacturing line and has an upper flat surface. The support member 12 is made from a plastic material having a low coefficient of friction so that the sheet 10 of unvulcanized rubber material is able to be slidably moved along the support member 12. In this embodiment, the sheet 10 has a thickness of 2 to 3 millimeters, and the support member 12 has a thickness of about 10 millimeters.

As shown in FIGS. 1 and 2A and 2B, two rotatable rollers 14 are provided, one of which is in contact with the sheet 10 of unvulcanized rubber material while the other is maintained in a lifted position, and vice versa. Each of the rollers 14 has a central shaft 16 extending perpendicular to the sheet feed direction m, and therefore, the roller 14 in contact with the sheet 10 of unvulcanized rubber material is rotated by the moving sheet 10 in the direction as shown by the arrow n. Simultaneously, a tackiness of sheet 10 of the unvulcanized rubber material acts on the roller 14 at a point T and provides a resistance to the rolling of the roller 14, whereby the roller 14 would be entrained in the sheet feed direction m if the roller 14 were able to move in that direction.

Each of rollers 14 is made from a metal, in particular, a stainless steel with a hard chromium plating, or a metal with a vulcanized rubber coating. Each of the rollers 14 has a diameter of 100 millimeters and a width of 50 millimeters. Note, although two rollers 14 are used in the illustrated embodiment, only one roller 14 can be used according to the present invention. The rollers 14 are rotatably mounted to the respective shafts 16 by bearing means (not shown), and the shafts 16 are secured to a pair of link arms 18 extending generally in parallel to the sheet feed direction m and in parallel to each other. An inverted T-shaped supporting link 20 comprises a pair of base portion 20a arranged outside the respective arms 18 and extending in parallel to the sheet feed direction m and in parallel to each other. The link arms 18 are pivotally supported at the center thereof by pins 19 (one seen in FIG. 2A) to the base portions 20a, so that one roller 14 is in contact with the sheet 10 of unvulcanized rubber material and the other roller 14 is maintained in a lifted position. The supporting link 20 also comprises an arcuate upright stand 20b extending transversely and interconnecting the base portions 20a together. Air cylinders 21 are pivoted to the top of the stand 20b and include downwardly extending piston rods 21a, respectively, which are connected to the link arm 18 by arcuate connecting members 21b with pivot pins 21c. The rollers 14 are brought into positions, as shown in FIGS. 1 and 2A, by extending one of the piston rods 21a and retracting the other piston rod 21a. Stoppers 90 are provided at the central bottom of the base portion to receive the linkage arms 18 during the pivotal motion thereof to thereby fix the linkage arms 18 to the supporting link 20. Also, arm stoppers 92 are provided on the floor to receive the supporting link 20 when the two rollers 14 are at the intermdediately lifted position during the pivotal movement of the link arms 18.

A cleaning roller 22 is rotatably supported at a portion of the stand 20b so that the cleaning roller 22 is in contact with the roller 14 in the lifted position. The cleaning roller 22 can contain a washing solution to thereby clean the surface of the lifted roller 14 before the next contact thereof with the moving sheet 10 of unvulcanized rubber material. In this way, it is possible to alternately effect a contact of the roller 14 with the moving sheet 10 and a cleaning of the roller 14, at constant intervals. To this end, engageable gears 94, 96 are coaxially provided with the rollers 14 and the cleaning roller 22, respectively, and an electric motor 98 drives the gear 94 of the cleaning roller 22. The number of teeth differs between the gears 94 and 96 to cause a difference in the surface velocity between the roller 14 and cleaning roller 22 to enhance cleaning effect. Also, cleaning solution is supplied through a supply pipe 99. The rotation of the cleaning roller 22 and the supply of the solution are carried out in synchronous with the pivotal movement of the link arms 18 during a predetermined time.

A measuring device 24 is connected to the base portion 20a of the supporting link 20 via a linkage rod 26 fixed to the rear of the base portion 20a of the supporting link 20. The measuring device 24 is fixedly carried on a stationary frame member F and measures a rolling resistance at the roller relative to the sheet 10 of unvulcanized rubber material. The measuring device 24 comprises a sensor for detecting a change of a position of the roller 14 rotated by the movement of the sheet 10 of unvulcanized rubber material in the sheet feed direction m as a function of an entraining force corresponding to a tackiness of the sheet 10 of unvulcanized rubber material, and outputting an electric signal when such a change is detected. Preferably, the measuring device 24 comprises a load cell with piezoelectric elements, or a differential transformer type sensor.

The output from the measuring device 24 is input to an electric controller 28, which controls a correcting means able to act on the surface of the sheet 10 of unvulcanized rubber material, to correct the tackiness of the sheet 10 of unvulcanized rubber material, in such a manner that the correcting means acts on the surface of the sheet 10 of unvulcanized rubber material when an output from the measuring device 24 is outside a predetermined range of tackiness, and does not act on the surface of the sheet 10 when an output from the measuring device 24 is within the predetermined range of tackiness.

Preferably, the correcting means comprises at least one brush 30 connected to the electric controller 28 through a drive circuit 32 and at least one gasoline-containing sponge swab 34 connected to the electric controller 28 through a drive circuit 36. The electric controller 28 outputs a control signal to the drive circuit 32 to operate the brush 30 (lower and lift same) to reduce a tackiness of the sheet 10 of unvulcanized rubber material when an output from the measuring device 24 is higher than an upper limit of the predetermined range of tackiness. Further, the electric controller 28 outputs a control signal to the drive circuit 36 to operate the gasoline containing sponge swab 34 (lower and lift same) to increase a tackiness of the sheet 10 of unvulcanized rubber material when an output from the measuring device 24 is lower than a lower limit of the predetermined range of tackiness. It is known in the art that brushing reduces a tackiness of unvulcanized rubber material and gasoline swabbing increases that tackiness. The brush 30 may be a nylon brush or a wire brush.

Movable support means are incorporated with the brush 30 and the swab 34, respectively, for bringing each of these correcting elements to an operative position at which the brush 30 or the swab 34 is in contact with the surface of the sheet 10 of unvulcanized rubber material, and to an inoperative position at which the brush 30 or the swab 34 is not in contact therewith.

Figure 4:
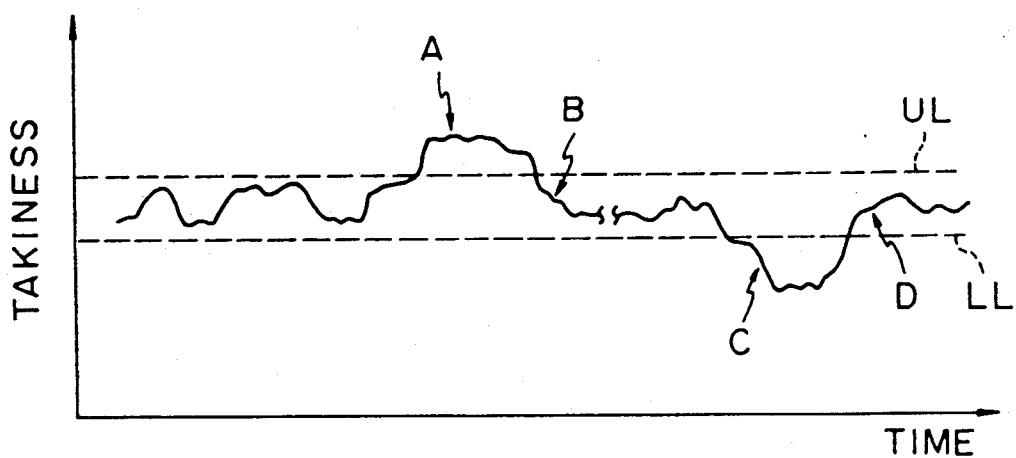
FIG. 4 is a graph showing an example of a tackiness measured and corrected by the device of FIG. 1.

FIG. 4 is a graph showing an example of the tackiness measured and corrected by the device of FIG. 1. As shown in FIG. 4, the curve shows a measured tackiness (a change of position of the roller 14) and an acceptable upper limit (UL) and lower limit (LL) of tackiness are empirically determined. The point A shows a start point of brushing, the point B shows a finish point of brushing, the point C shows a start point of swabbing, and the point D shows a finish point of swabbing. Note, points A to D are slightly behind the points at which the curve intersects the upper limit (UL) or the lower limit (LL), to avoid a hunting of the control.

Figure 5:
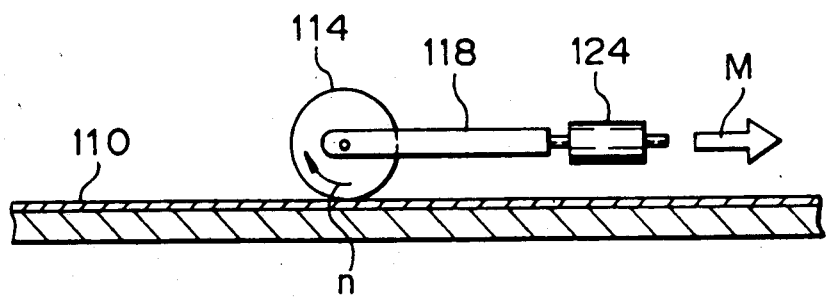
FIG. 5 is a view illustrating a rolling resistance.

It has been recognized that the principle of measuring a tackiness according to the present invention corresponds to that in FIG. 5, in which a sheet 110 is stationary and a roller 114 is driven in the direction of the arrow M. The roller 114 will rotate in the direction of the arrow n and a rolling resistance will arise between the roller 114 and the sheet 110 in accordance with the surface conditions thereof. A measuring device 124 is connected to the roller 114 via a link 118 and measures the rolling resistance, which is representative of the tackiness of the sheet 110.

Figure 2:
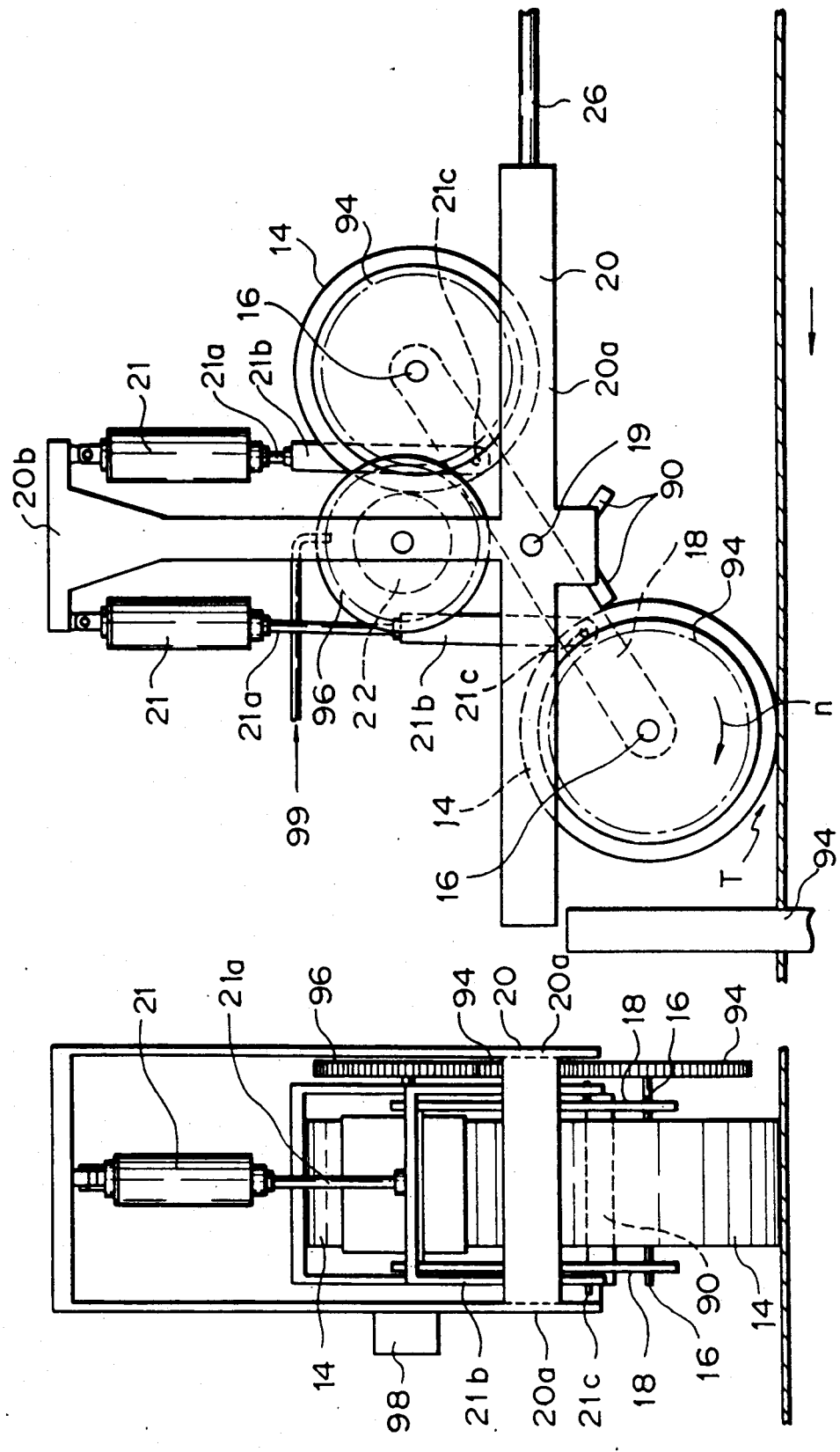
FIG. 2A is a side elevational view of a portion of the device of FIG. 1, shown on an enlarged scale.
FIG. 2B is a front elevational view of the device of FIG. 2A.
Figure 3:
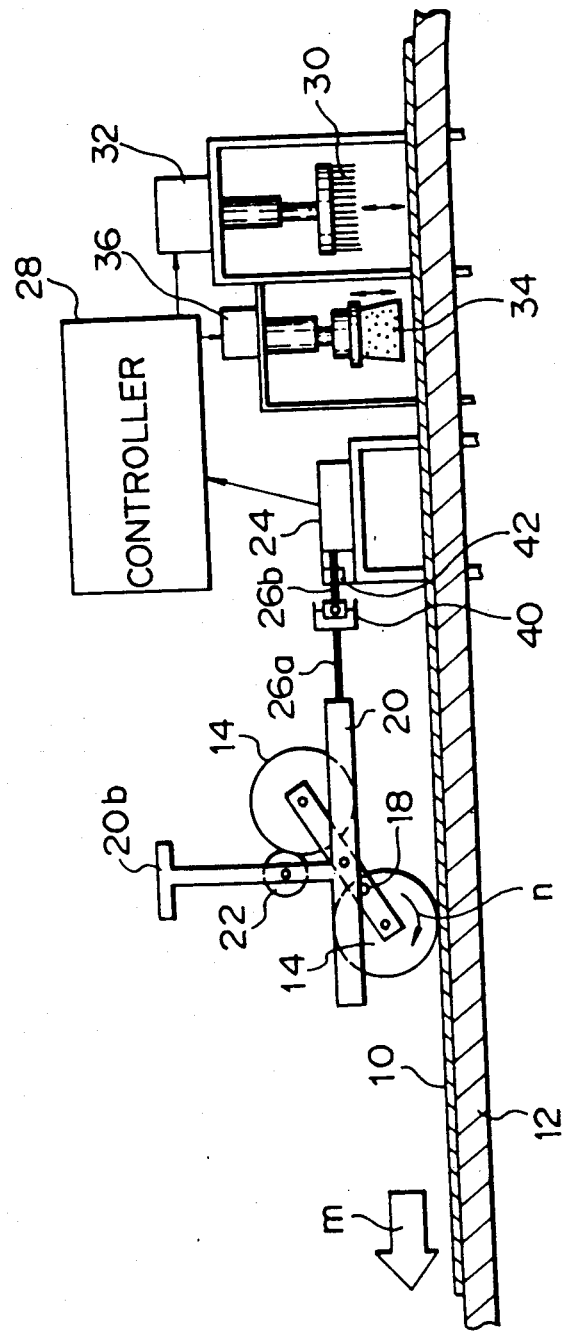
FIG. 3 is a side elevational view of a device for continuously measuring and correcting a tackiness of a sheet of unvulcanized rubber material according to the second embodiment of the present invention.

FIG. 3 shows the second embodiment of the present invention. Elements in FIG. 3 similar to those of FIGS. 1 and 2 are given the same reference numerals. In FIG. 3, a first rod 26a and a second rod 26b are provided to connect the rear of the base portion 20a (see FIG. 2) of the supporting link 20 to the measuring device 24, in place of the linkage rod 26 shown in FIGS. 1 and 2. The first and second rods 26a and 26b extend linearly, and the extreme end of the second rod 26b is connected to the measuring device 24. A universal joint 40 interconnects the first and second rods 26a and 26b, and a linear bearing 42 slidably supports the second rod 26b at the stationary frame member F, whereby the measuring device 24 receives only a linear movement of the second rod 26b caused by a movement of the roller 14.

Figure 6:
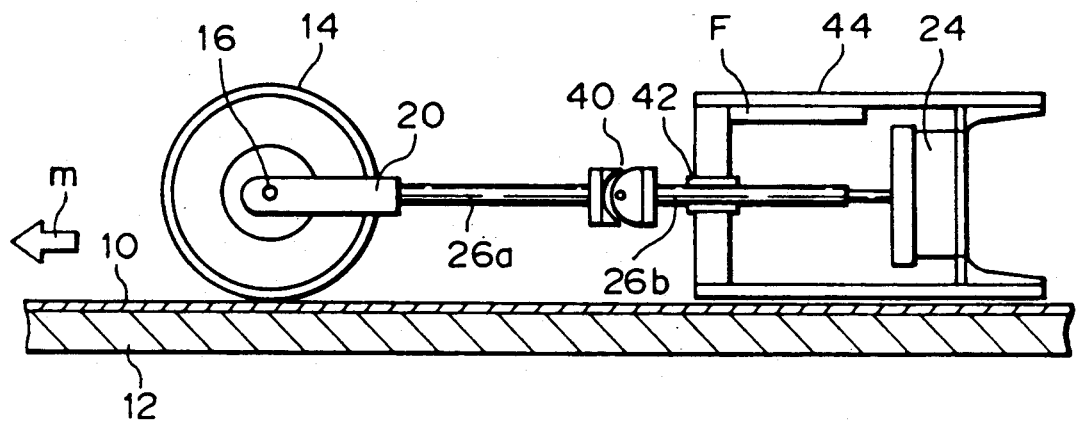
FIG. 6 is a side elevational view of a device for continuously measuring and correcting a tackiness of a sheet of unvulcanized rubber material according to the third embodiment of the present invention.
Figure 7:
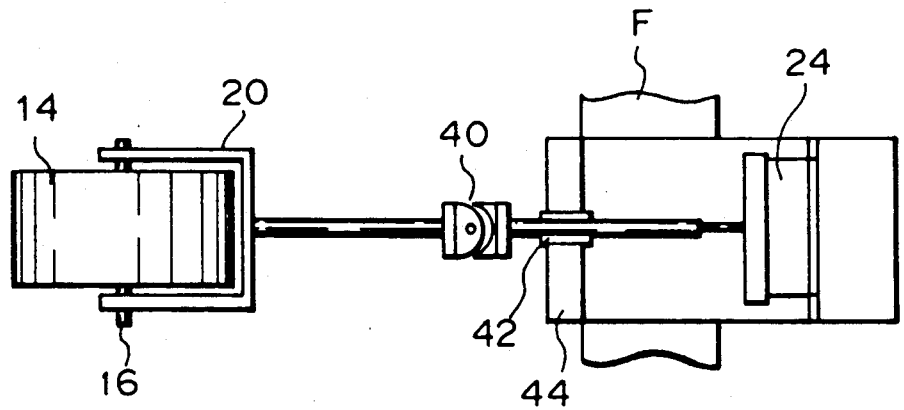
FIG. 7 is a plan view of the device of FIG. 6.

FIG. 6 and 7 show the third embodiment of the present invention. In this embodiment, the inventive device includes a single roller 14 in contact with a sheet 10 of unvulcanized rubber material. The roller 14 is connected to a measuring device 24 via a supporting link 20 and first and second rods 26a and 26b interconnected by a universal joint 40. The measuring device 24 is mounted in a housing 44 which is fixed to the stationary frame member F. A linear bearing 42 is attached to the housing 44 and the second rod 26b is slidably supported in the linear bearing 42. The measuring device 24 can be connected to an electric controller (not shown in FIGS. 6 and 7, refer to FIG. 1) and correcting means (not shown in FIGS. 6 and 7, refer to FIG. 1).

Figure 8:
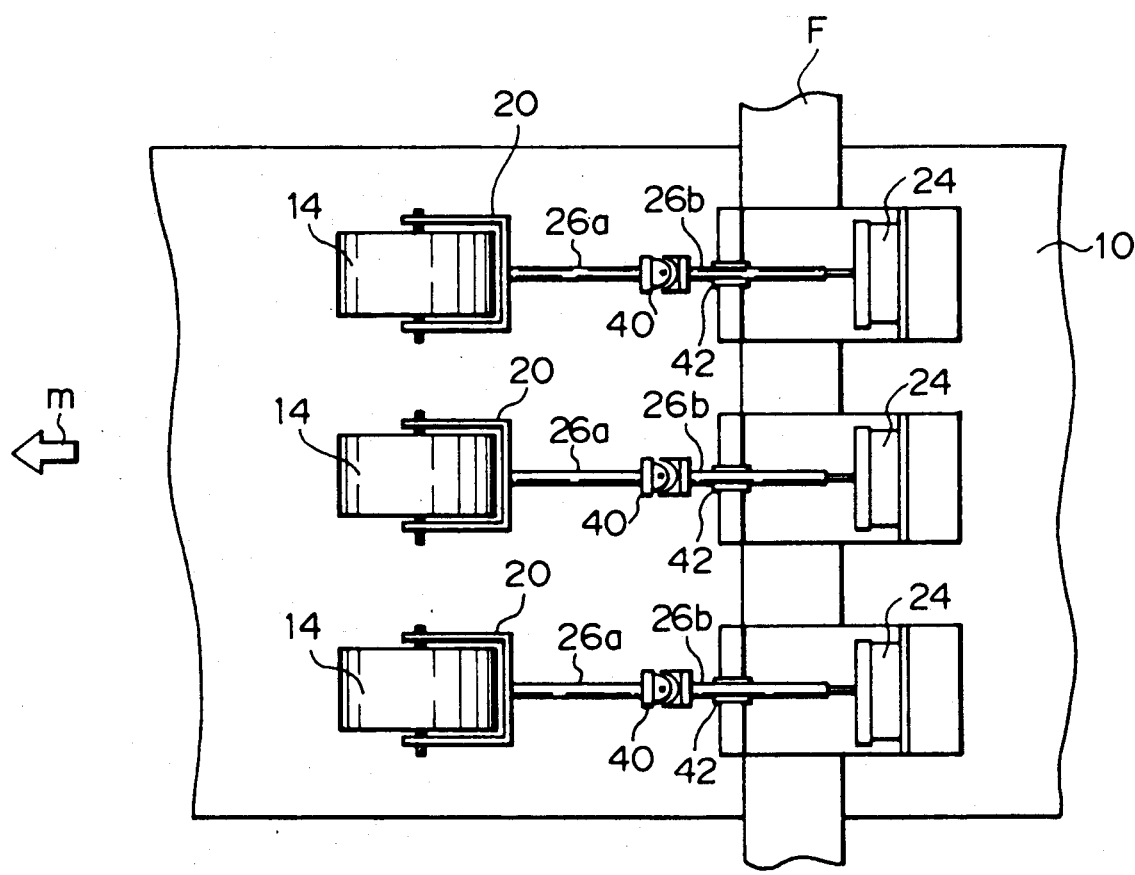
FIG. 8 is a plan view of a device for continuously measuring and correcting a tackiness of a sheet of unvulcanized rubber material according to the fourth embodiment of the present invention.

FIG. 8 shows the fourth embodiment of the present invention. In this embodiment, the inventive device includes three rollers 14 arranged transversely across the sheet 10 of unvulcanized rubber material. Each of the rollers 14 is associated with respective linkage means 20, 26a, and 26b and a measuring device 24, each measuring unit having a constructed similar to that of the device shown in FIG. 6.

Figure 9:
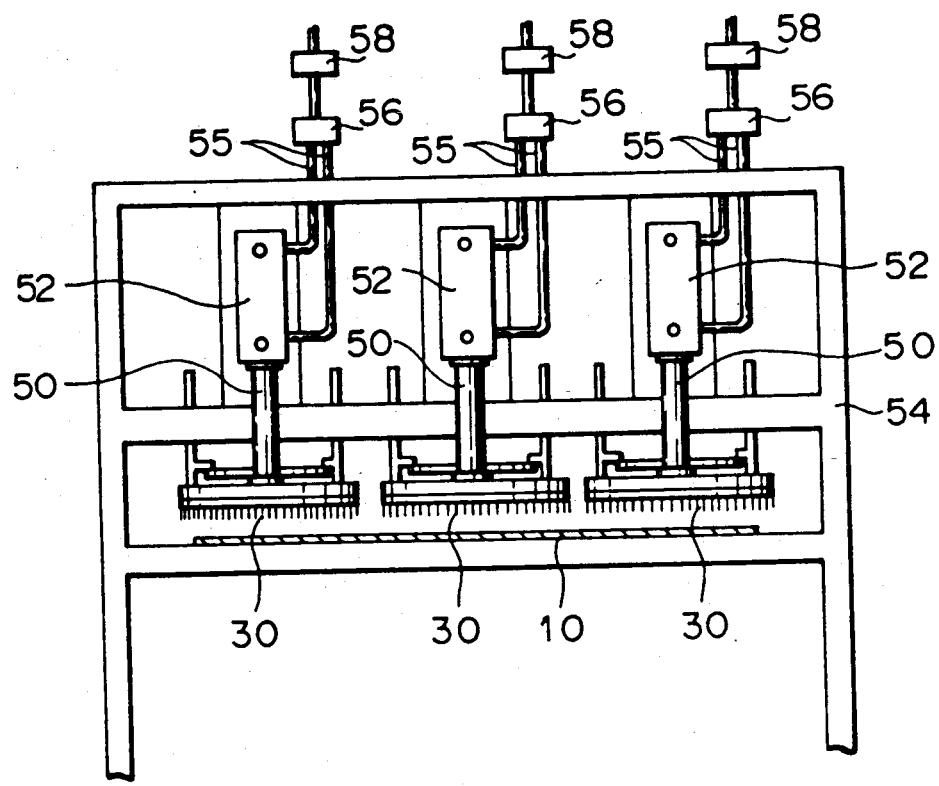
FIG. 9 is a front elevational view of a brushing arrangement used in the device of FIG. 8, for correcting a tackiness of a sheet of unvulcanized rubber material.
Figure 10:
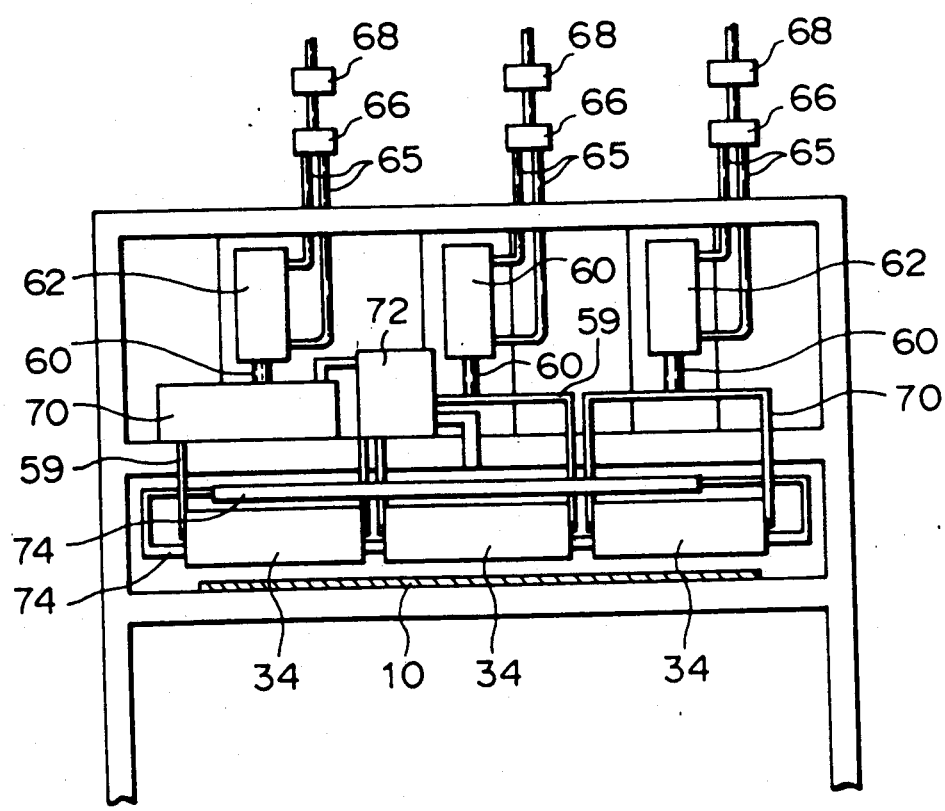
FIG. 10 is a front elevational view of a gasoline swab arrangement used in the device of FIG. 8 for correcting a tackiness of a sheet of unvulcanized rubber material.

This measuring arrangement is used in combination with a brushing arrangement of FIG. 9 and a swab arrangement of FIG. 10.

As shown in FIG. 9, three brushes 30 are arranged transversely across the sheet 10 of unvulcanized rubber material, in a manner similar to the rollers 14 shown in FIG. 8, and as shown in FIG. 10, three gasoline containing sponge swabs 34 are similarly arranged transversely across the sheet 10 of unvulcanized rubber material. Accordingly, each of the brushes 30 and the sponge swabs 34 can be operated independently in response to an output from the corresponding measuring device 24.

As shown in FIG. 9, each of the brushes 30 is attached to a piston rod 50 of a pneumatic cylinder 52 fixed to a housing 54, and pipes 55 are connected to the ends of the pneumatic cylinder 52 to supply compressed air from a source (not shown) via a flow control valve 56 and a pressure control valve 58, so that each of the brushes 30 can be independently operated and the operating pressure thereof can be varied in accordance with the output from the measuring device 24.

As shown in FIG. 10, each of the sponge swabs 34 is attached to a control arm 59, which is attached to a piston rod 60 of a pneumatic cylinder 62 fixed to a housing 64, and pipes 65 are connected to the ends of the pneumatic cylinder 62 to supply compressed air from a source (not shown) via a flow control valve 66 and a pressure control valve 68, so that each of the sponge swabs 34 can be independently operated and the operating pressure thereof can be varied in accordance with the output from the measuring device 24. Further, a gasoline tank 70 and a delivery pump 72 are provided, and nozzles 74 are connected to the delivery pump 72 and arranged on either side of the sponge swabs 34. The delivery pump 72 can be operated just before the operation of the sponge swabs 34.

As explained above, a device for continuously measuring and correcting a tackiness of sheet of a rubber material, according to the present invention, includes an automatic measuring means for continuously measuring a tackiness of sheet of an unvulcanized rubber material by detecting a resistance to a rolling of a roller rotating on the surface of a moving sheet of the unvulcanized rubber material, and correcting means for correcting a tackiness of the sheet of unvulcanized rubber material to a value within a predetermined range of tackiness when an output from the measuring means is outside the predetermined range of tackiness. Therefore, it is possible to continuously measure a tackiness of an unvulcanized rubber material, and to provide the unvulcanized rubber material with an appropriate tackiness. As a result, an abnormal situation can be corrected even at an unmanned line, and the device can be used in a rubber manufacturing line since sampling is not necessary and the tackiness testing is carried out without the need to cut the material into sample pieces.

We claim:

1. A device for continuously measuring and correcting a tackiness of sheet of rubber material, comprising:

feeding means for continuously feeding a sheet of unvulcanized rubber material along a predetermined path and in a predetermined direction;

at least one rotatable roller in contact with said sheet of unvulcanized rubber material and having a central shaft extending perpendicular to said predetermined feeding direction;

linkage means having a first end and a second end, said first end being connected to said shaft of said roller;

measuring means arranged at a fixed position on a stationary frame member and connected to said second end of said linkage means for measuring a rolling resistance of said roller relative to said sheet of unvulcanized rubber material when said roller is in contact with said sheet of unvulcanized rubber material, said rolling resistance representing a degree of tackiness of said sheet of unvulcanized rubber material;

correcting means able to act on the surface of said sheet of unvulcanized rubber material for correcting a tackiness of said sheet of unvulcanized rubber material; and control means for controlling said correcting means in response to an output from said measuring means in such a manner that said correcting means acts on the surface of said sheet of unvulcanized rubber material when an output from said measuring means is outside a predetermined range of tackiness and does not act on the surface of said sheet of unvulcanized rubber material when an output from said measuring means is within said predetermined range of tackiness.

2. A device according to claim 1, wherein said control means outputs a first control signal when an output from said measuring means is higher than an upper limit of said predetermined range of tackiness and a second control signal when an output from said measuring means is lower than a lower limit of said predetermined range of tackiness, and wherein said correcting means comprises a first correcting means for reducing a tackiness of said sheet of unvulcanized rubber material based on said first control signal and a second correcting means for increasing a tackiness of said sheet of unvulcanized rubber material based on said second control signal.

3. A device according to claim 2, wherein said first correcting means comprises at least one brush and a movable support means thereof for moving said brush between an operative position and an inoperative position thereof.

4. A device according to claim 2, wherein said second correcting means comprises at least one gasoline containing swab and a movable support means thereof for moving said brush between an operative position and an inoperative position thereof.

5. A device according to claim 1, wherein said measuring means comprises a sensor for detecting a change of a position of said roller in said predetermined direction as a function of a force produced in accordance with a tackiness of said sheet of unvulcanized rubber material, and outputting an electric signal when such a change is detected.

6. A device according to claim 5, wherein said measuring means comprises a load cell with piezoelectric elements.

7. A device according to claim 5, wherein said measuring means comprises a differential transformer type sensor.

8. A device according to claim 1, wherein said first end of said linkage means comprises a pair of arms extending in parallel to each other, said arms being connected to opposite ends of said shaft of said roller, respectively.

9. A device according to claim 8, wherein said roller is rotatably mounted on said shaft by a bearing means.

10. A device according to claim 8, wherein said linkage means includes a rear portion comprising a first rod and a second rod extending linearly so that said second rod provides said second end of said linkage means, a universal joint interconnecting said first and second rods, and a linear bearing slidably supporting said second rod on said stationary frame member, whereby said measuring means receives only a linear movement of said second rod in accordance with a movement of said roller.

11. A device according to claim 10, wherein said second rod extends generally in parallel to said predetermined feeding direction.

12. A device according to claim 1, wherein said at least one roller comprises a pair of spaced rollers, and said linkage means comprises at least one first linkage member having opposite ends supporting said rollers, respectively, and a second linkage member having opposite ends, one of the ends of said second linkage member pivotally supporting said first linkage member so that one of said rollers is brought in contact with said sheet of unvulcanized rubber material and the other roller is maintained at a lifted position at which it is not in contact with said sheet, the other end of said second linkage member being connected to said measuring means.

13. A device according to claim 1, wherein said at least one roller comprises a plurality of rollers arranged transversely across said sheet of unvulcanized rubber material, each of said rollers being associated with a respective linkage means and measuring means.

14. A device according to claim 13, wherein a plurality of said correcting means for correcting a tackiness of said sheet of unvulcanized rubber material are arranged transversely across said sheet of unvulcanized rubber material, each of said correcting means corresponding to an associated one of said plurality of rollers.

15. A device according to claim 1, wherein a portion of said predetermined path is formed by a stationary support member having an upper flat surface on which said sheet of unvulcanized rubber material is able to be slidably moved, said at least one roller being brought into contact with said sheet of unvulcanized rubber material over said upper flat surface.

* * * * *